(12) United States Patent
Blanche

(10) Patent No.: US 12,290,488 B2
(45) Date of Patent: May 6, 2025

(54) METHOD AND APPARATUS FOR THE TREATMENT OF CELLULITE WITH THE COMBINATION OF LOW LEVEL LIGHT, ULTRASOUND, AND VACUUM

(71) Applicant: Raymond R. Blanche, Chatham, NJ (US)

(72) Inventor: Raymond R. Blanche, Chatham, NJ (US)

( * ) Notice: Subject to any disclaimer, the term of this patent is extended or adjusted under 35 U.S.C. 154(b) by 778 days.

(21) Appl. No.: 17/479,486

(22) Filed: Sep. 20, 2021

(65) Prior Publication Data

US 2022/0062093 A1 Mar. 3, 2022

Related U.S. Application Data

(63) Continuation-in-part of application No. 15/497,697, filed on Apr. 26, 2017, now Pat. No. 11,123,577.

(60) Provisional application No. 62/327,731, filed on Apr. 26, 2016.

(51) Int. Cl.
*A61H 9/00* (2006.01)
*A61N 5/06* (2006.01)
*A61N 7/00* (2006.01)

(52) U.S. Cl.
CPC ......... *A61H 9/0057* (2013.01); *A61N 5/0616* (2013.01); *A61N 7/00* (2013.01); *A61H 2201/10* (2013.01); *A61H 2207/00* (2013.01); *A61N 2005/0652* (2013.01); *A61N 2005/0659* (2013.01); *A61N 2005/0663* (2013.01); *A61N 2007/0008* (2013.01)

(58) Field of Classification Search
CPC .............. A61H 9/0057; A61H 2201/10; A61H 2201/1207; A61H 2201/5002; A61H 2201/0153; A61H 2201/105; A61H 2207/00; A61N 5/0616; A61N 7/00; A61N 2005/0652; A61N 2005/0659; A61N 2005/066; A61N 2005/0644; A61N 2005/0662; A61N 2007/0008; A61N 2007/0034; A61B 2018/00291; A61B 2018/00464

See application file for complete search history.

(56) References Cited

U.S. PATENT DOCUMENTS

| | | | |
|---|---|---|---|
| 4,930,504 A | * | 6/1990 | Diamantopoulos .. A61N 5/0616 250/494.1 |
| 6,319,211 B1 | | 11/2001 | Ito et al. |
| 6,511,445 B2 | | 1/2003 | Sivan et al. |
| 6,743,215 B2 | | 6/2004 | Bernabei |
| 6,911,031 B2 | | 6/2005 | Muldner |

(Continued)

FOREIGN PATENT DOCUMENTS

WO WO2008127641 10/2008

*Primary Examiner* — Sean D Mattson
(74) *Attorney, Agent, or Firm* — McHale & Slavin, P.A.

(57) ABSTRACT

A method and device is taught to improve the appearance of cellulite by combining mild exfoliation of the skin, various wavelengths of low level light, ultrasound, and a vacuum or suction. The device is intended to increase the metabolic rate of the fat cells and reduce their size, while increasing the extensibility or length of the septae. Such increased activity will promote blood flow to the affected area thereby increasing cell nutrients and removing cellular exudates while stimulating the growth of new collagen thereby alleviating the cellulite.

15 Claims, 12 Drawing Sheets

(56) References Cited

U.S. PATENT DOCUMENTS

| | | | |
|---|---|---|---|
| 2003/0032900 A1* | 2/2003 | Ella | A61N 5/0616 |
| | | | 601/123 |
| 2004/0260210 A1 | 12/2004 | Ella et al. | |
| 2005/0251117 A1 | 11/2005 | Anderson | |
| 2006/0259102 A1* | 11/2006 | Slatkine | A61B 17/205 |
| | | | 607/88 |
| 2007/0198004 A1* | 8/2007 | Altshuler | A61N 5/0616 |
| | | | 606/9 |
| 2008/0167585 A1 | 7/2008 | Khen et al. | |
| 2008/0215039 A1* | 9/2008 | Slatkine | A61M 5/425 |
| | | | 606/9 |
| 2008/0243039 A1 | 10/2008 | Rhoades et al. | |
| 2009/0093864 A1 | 4/2009 | Anderson | |
| 2009/0146086 A1 | 6/2009 | Manstein | |
| 2010/0274329 A1 | 10/2010 | Bradley et al. | |
| 2011/0040235 A1* | 2/2011 | Castel | A61F 7/00 |
| | | | 604/20 |
| 2011/0046523 A1* | 2/2011 | Altshuler | A61N 7/02 |
| | | | 601/3 |
| 2012/0265044 A1 | 10/2012 | Broens | |
| 2013/0184693 A1* | 7/2013 | Neev | A61N 5/0616 |
| | | | 606/9 |
| 2013/0345670 A1 | 12/2013 | Rajagopalan et al. | |
| 2014/0025050 A1 | 1/2014 | Anderson | |
| 2015/0045723 A1* | 2/2015 | Paithankar | A61P 17/10 |
| | | | 604/22 |
| 2017/0348539 A1* | 12/2017 | Schwarz | A61N 1/328 |

* cited by examiner

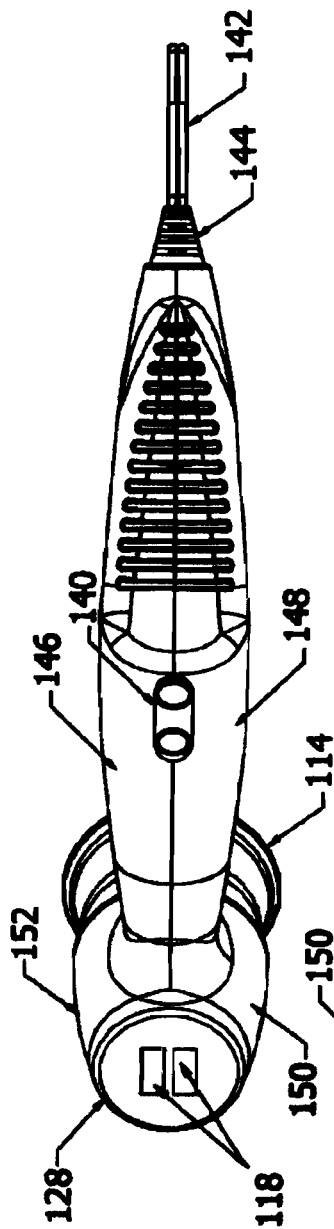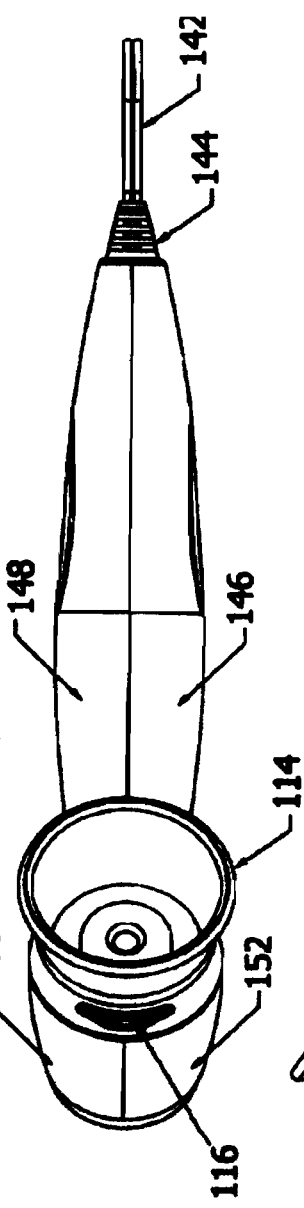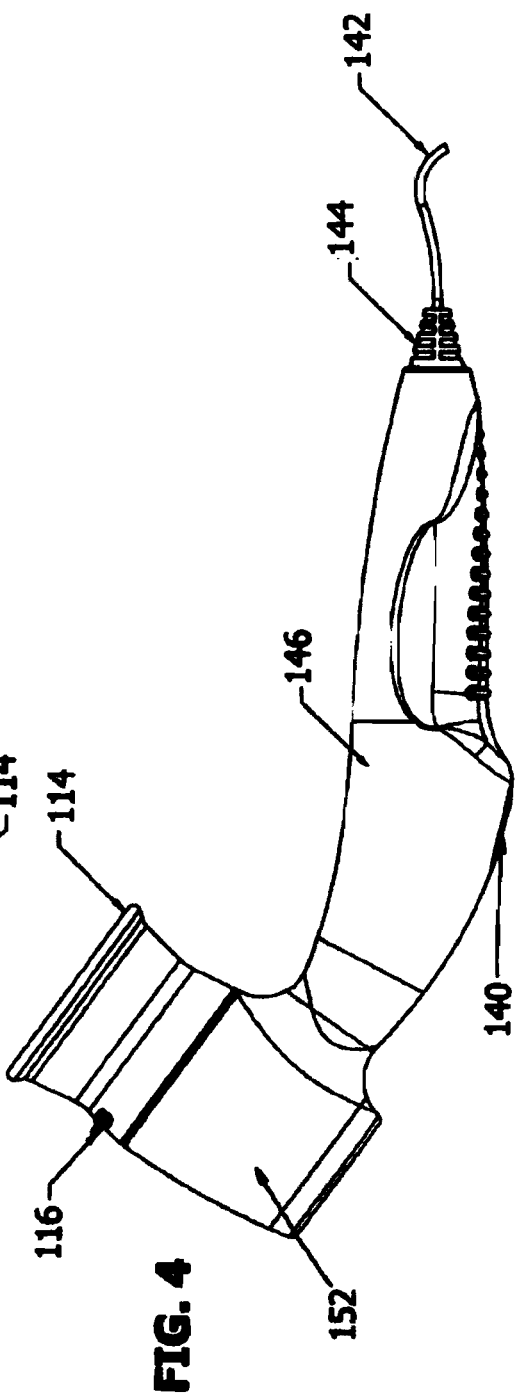

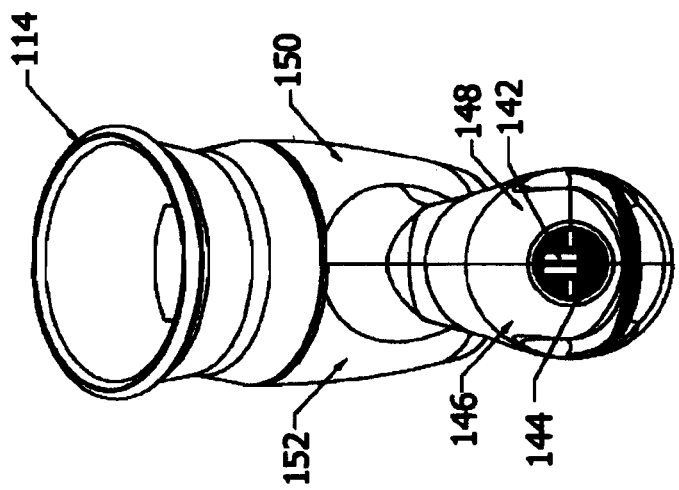
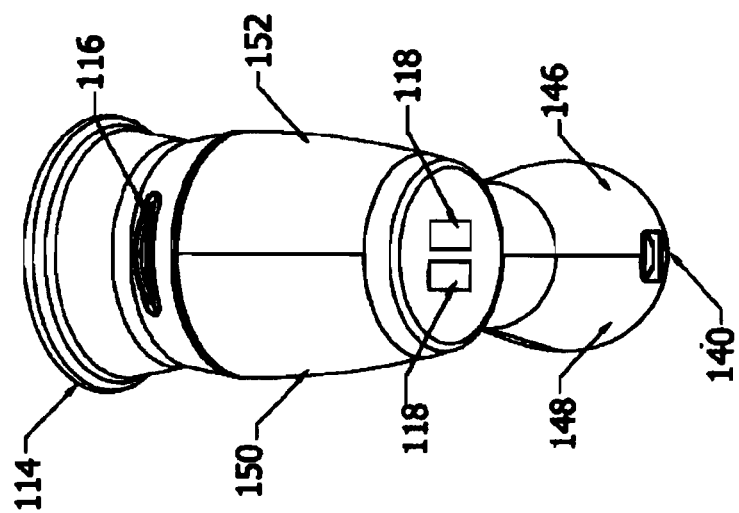

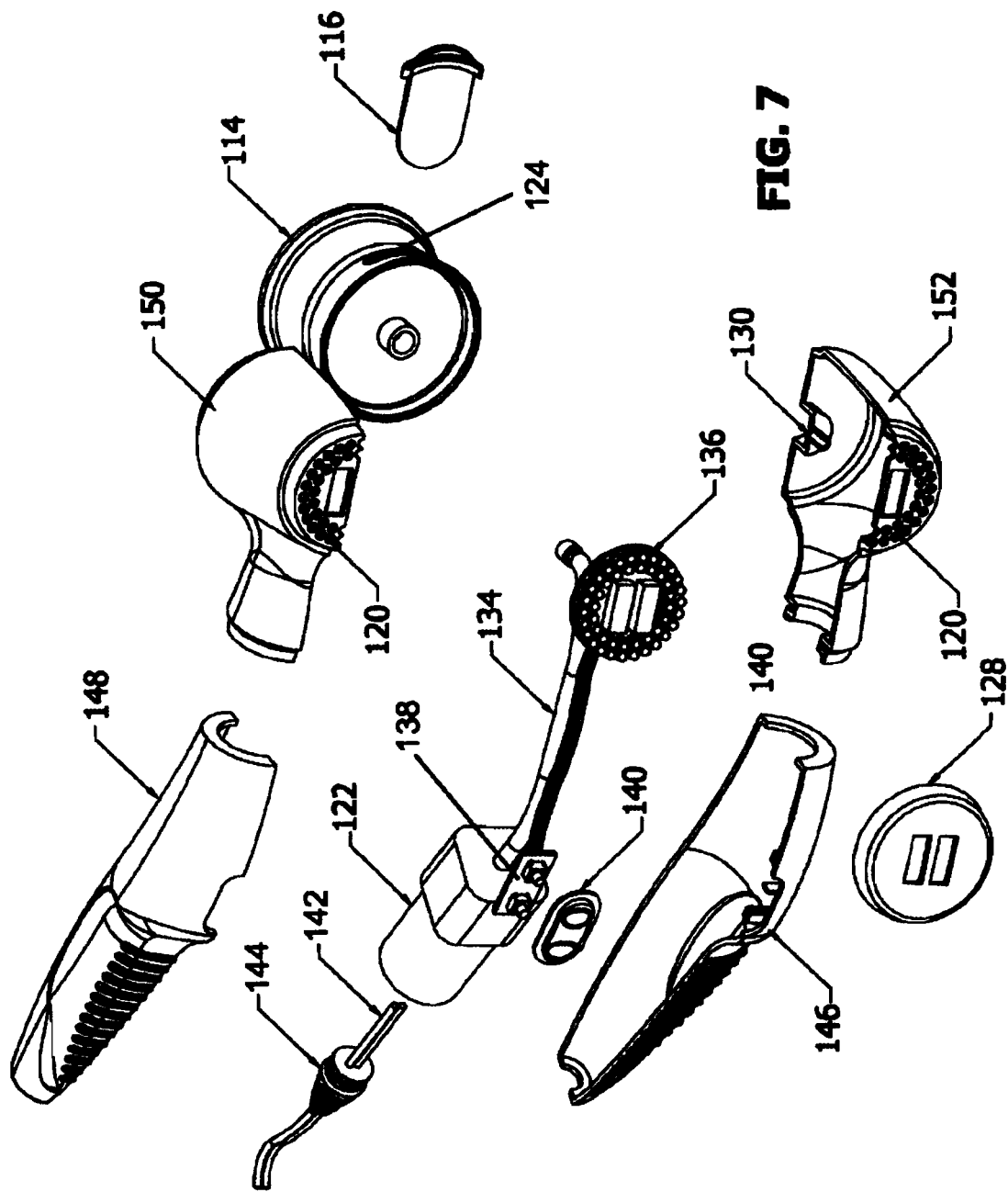

METHOD AND APPARATUS FOR THE TREATMENT OF CELLULITE WITH THE COMBINATION OF LOW LEVEL LIGHT, ULTRASOUND, AND VACUUM

REFERENCE TO RELATED APPLICATIONS

In accordance with 37 C.F.R. 1.76, a claim of priority is included in an Application Data Sheet filed concurrently herewith. Accordingly, this is a continuation-in-part application of U.S. patent application Ser. No. 15/497,697, entitled "METHOD AND APPARATUS FOR THE TREATMENT OF CELLULITE WITH THE COMBINATION OF LOW LEVEL LIGHT, ULTRASOUND, AND VACUUM", filed on Apr. 26, 2017, which claims priority to U.S. Provisional Application No. 62/327,731, entitled "METHOD AND APPARATUS FOR THE TREATMENT OF CELLULITE WITH THE COMBINATION OF LOW LEVEL LIGHT, ULTRASOUND, AND VACUUM", filed on Apr. 26, 2016. The contents of the above referenced applications are incorporated herein by reference in their entirety.

FIELD OF THE INVENTION

The field of the embodiments of the present invention relate to a method and process to improve the appearance of cellulite by combining mild exfoliation of the skin, various wavelengths of low level light, ultrasound, and mild vacuum.

BACKGROUND OF THE INVENTION

Cellulite, or dimpling of the skin, is very common, particularly in women, and not always related to excessive weight. Cellulite is a herniation of enlarged subcutaneous fat interspersed with fibrous connective tissue (septae) that gives rise to such dimpling. These enlarged fat cells expand to a point that the connective septae can no longer stretch. This restriction of the septae causes a dimpling effect in the skin which is often called an "orange peel" effect or "mattress" effect. Cellulite may also cause a restriction of blood flow to and out of the affected area, as well as restrictive lymphatic movement. Due to the prevalence in women, and more particularly women of certain races, there are indications that the cause of cellulite is physiological rather than pathological.

Cellulite is hard to treat and cannot be dealt solely with diet and exercise. Treatment for cellulite often requires changing the metabolic processes in the afflicted area(s). There have been attempts to disrupt or change such metabolic processes including devices with rollers that would knead the skin and stretch the skin. However, if the skin was too traumatized by the kneading and rolling, the "treatment" could lead to more adhesions and even exacerbate the appearance of the cellulite.

In response, various thermal elements have been implemented which heat the skin and allow for more efficient stretching of the skin and connective tissues. This approach, while more logical, made treatments even more technique dependent.

Surgical intervention is also an option. In some instances, the surgeon will cut the connective, fibrous septae with a sharp blade or laser. This would instantly remove surface tension created by the shortened, tight septae. However, even this process has downsides as the skin loses some of its "anchoring" to the musculature below and there is an increased risk to create scar tissue. Finally, many topicals (creams) have been produced to address cellulite that fall short of expectations, or fail to show any results, when used as a standalone treatment. Review of related technology:

U.S. Pat. No. 6,743,215 pertains to application of electrical pulses and mechanical vibrations to the skin in a controlled manner, in order to increase the absorption of substances applied previously on the skin. A dermabrasion treatment is first performed on a region of the skin to be later given a skin absorption enhancement treatment. After the dermabrasion treatment, electrical pulses are provided to the skin by way of an array of electrodes disposed on a vibrating head, and the mechanical vibrations are provided to the skin by way of the vibrating head being made to vibrate. Preferably, the electrical and mechanical vibrations are at the same frequency and phase with respect to each other, in order to increase the absorption effect. Also, a suction may be applied to the skin, in order to provide for a substantially uniform absorption of the substance that was applied previously on the skin.

U.S. Pat. No. 6,511,445 pertains to a cellulite massage system that includes a body having a bottom surface, means for producing suction to create a massage action at the bottom surface, and a built-in gel dispenser in said body for dispensing gel to the bottom surface. The invention also provides a method for treating the appearance of cellulite including the steps of applying suction to an area of a body containing cellulite so as to massage that area, and applying gel to that area so as to improve the texture and look of skin on the treated area of the body.

U.S. Patent Application 2014/0025050 pertains to methods and an apparatus for heating up a surface of a skin area that is to undergo a topical treatment. There is a method of placing a device enabled with vacuum suction pressure on a surface of a tissue area to be treated or applying a vacuum suction pressure on the surface of the skin area to pull up the skin area, and an underlying tissue into an aperture opening of the device. Simultaneously, while retaining vacuum suction, the apparatus heats up a volume of tissue that is pulled up inside the aperture opening of the device such that the temperature of the tissue area rises to an elevated ambient temperature and performing a desired treatment, through an energy-generating module, on the tissue volume after the tissue area has been heated up.

U.S. Patent Application 2009/0093864 pertains to methods, systems, and devices to treat a region of skin; the treatment may be used to stimulate the production of collagen or destroy adipose tissue. The region of skin is exposed to a uniform energy application or series of applications. The region of skin may be exposed to positive and negative pressures. Therapeutic substances may be applied to the region of skin.

International Application WO2008/127641 pertains to methods for applying a first and second wavelength of low intensity light therapy to a target area of a subject for various treatments including promoting collagen production, increasing blood flow, decreasing wrinkles, and reducing fat and/or cellulite. The methods can optionally be combined with massaging the tissue or modulating or pulsing the otherwise continuous wave.

Thus, various devices and methodologies are known in the art. However, their structure and means of operation are substantially different from the present disclosure. The other inventions also fail to solve all the problems taught by the present disclosure. At least one embodiment of this invention is presented in the drawings below and will be described in more detail herein.

SUMMARY OF THE INVENTION

With the physical effects and potential psychological effects of cellulite in mind, a goal of embodiments of the present invention is to increase the metabolic rate of the fat cells and reduce their size, while increasing the extensibility or length of the septae. Such increased activity will promote blood flow to the affected area thereby increasing cell nutrients and removing cellular exudates while stimulating the growth of new collagen.

Thus, the present invention and its embodiments teach and describe an apparatus and method that logically and cost effectively treats cellulite with an "at home" device to be used by the consumer. Its inherent design is safe, easy to use, and a practical way to treat the appearance of cellulite.

The process may begin with an exfoliation of the area to be treated. The exfoliation allows an applied topical agent to better penetrate the skin by removing the natural barrier of the stratum corneum. Light sources or light emitting diodes (LEDs) present on the device may then be used on the exfoliated area. The light sources of the device are configured to emit particular wavelength(s) to target particular cell receptors and subcellular mitochondrial components to induce pro-collagen synthesis.

Ultrasound may be used on conjunction with the light sources to create a pathway for the topical agent to better penetrate by increasing cellular permeability. The combination of the energies and chemistry create an effective synergy leading to results that are superior to those known in the art. Further, a vacuum feature of the device may be applied to mechanically yet gently stretch the connective tissue or septae and further increase blood flow to the affected area.

In one embodiment of the present invention there is a cellulite disrupting apparatus having a handle with a first end and a second end; and a head coupled to the first end of the handle, the head having at least a first side and a second side, wherein the first side comprises a cup having a filter positioned therein, the filter being permeable to gases; and wherein the second side comprises a plurality of light sources and at least one ultrasonic transducer.

In another embodiment of the present invention there is a cellulite disrupting apparatus having a handle with a first end and a second end; a head disposed on the first end of the handle, the head having at least a first side and a second side, wherein the first side has a removable cup coupled thereto, and wherein the second side has a plurality of light sources and at least one ultrasonic transducer, wherein the plurality of light sources and the at least one ultrasonic transducer are covered by an optically clear covering; a vacuum port disposed in the first side of the head, wherein the vacuum port is configured to be selectively covered by a filter; and a vacuum tube having a first end and a second end, wherein the first end of the vacuum tube is coupled to the vacuum port and the second end of the vacuum tube is coupled to a motor.

In general, the present invention succeeds in conferring the following, and others not mentioned, benefits and objectives.

It is an object of the present invention to provide an apparatus that stretches or lengthens the septae of a user.

It is an object of the present invention to provide an apparatus allows for transdermal applications of topical creams, ointments, gels, etc.

It is an object of the present invention to provide an apparatus that increases blood flow to a targeted area.

It is an object of the present invention to provide an apparatus that creates a synergistic effect between light therapies and ultrasonic wave therapies.

It is an object of the present invention to provide an apparatus that increases the metabolic rate of subcutaneous fat cells.

It is an object of the present invention to provide an apparatus that is safe and easy to use.

It is an object of the present invention to provide an apparatus that is lightweight and inexpensive.

It is an object of the present invention to provide an apparatus that may be used by the consumer in their home.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 illustrates a top view of an embodiment of the present invention.

FIG. 3 illustrates a bottom view of an embodiment of the present invention.

FIG. 4 illustrates a side view of an embodiment of the present invention.

FIG. 5 illustrates a front view of an embodiment of the present invention.

FIG. 6 illustrates a back view of an embodiment of the present invention.

FIG. 7 illustrates an exploded parts view of an embodiment of the present invention.

DETAILED DESCRIPTION OF THE INVENTION

Figure 1:
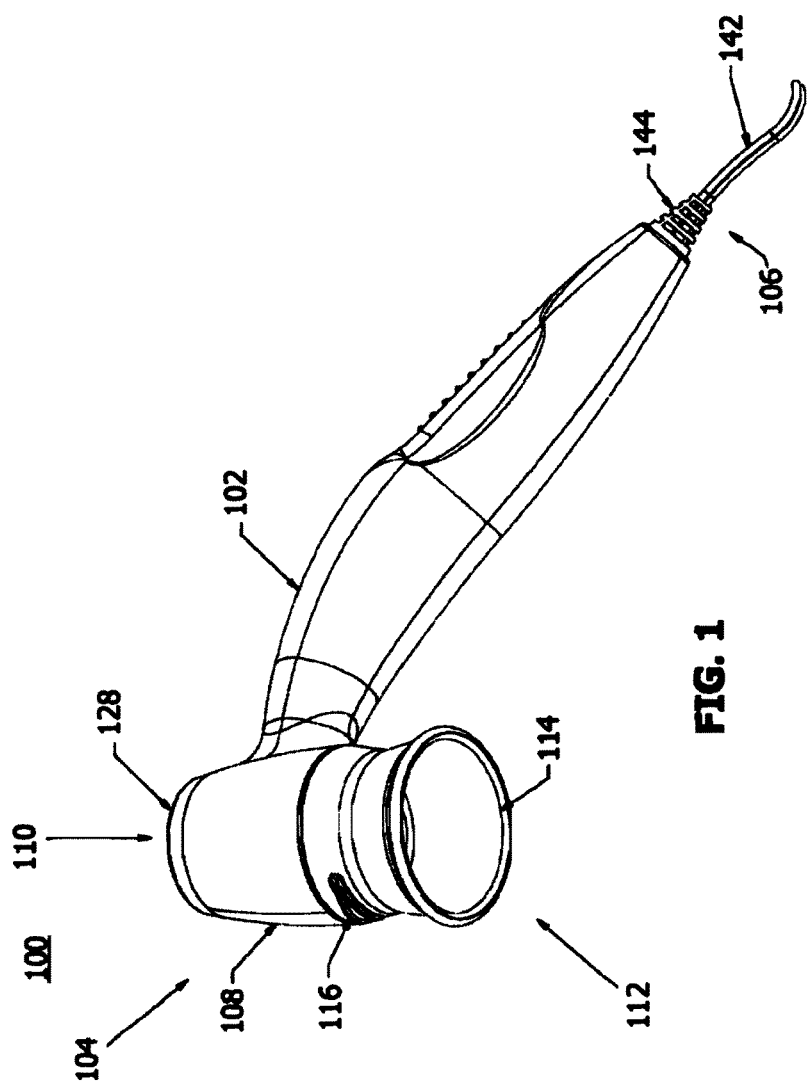
FIG. 1 illustrates a perspective view of an embodiment of the present invention.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto. As used herein, the term "about" refers to a numerical value or range that is up to 20% above or below the stated numerical value or range.

Referring now to FIGS. 1-8, there is an embodiment of the present invention. The device 100 generally has a handle 102, a head 108, removable cup 114, bottom 112 of head 108, top 110 of head 108, optically clear covering 128, first end 104, second end 106, power cord 144, power cord anchor 142, filter 116, depressible buttons 140, light sources 120, ultrasonic transducer 118, left side 150 of head 108, right side 152 of head 108, main printed circuit board 136, button printed circuit board 138, left side 148 of handle 102, slot 124, right side 146 of handle 102, vacuum motor 122, vacuum tube 134, and vacuum port 130.

The handle 102 may be generally smooth and polygonal or may be ergonomically configured to support a hand gripping said handle 102. For example, there may be ergonomic finger placement areas to facilitate grip and ease of use. The handle 102 may also have switches or buttons 140 (see FIG. 7) that control its operational state. Such buttons 140 may allow one to change operational modes of the device 100 as well as control its on/off state.

The head 108 may be configured to be dual sided in that each side (top 110, bottom 112) of the head 108 may have operational components. In some embodiments, the functional components are all located on a single side of the head 108, and in other embodiments, the functional components may be located on more than two sides (e.g. top, side, bottom, etc.). The functional components may comprise but are not limited to light sources 120, ultrasonic crystals (transducers) 118, vacuums (see vacuum tube 134 and motor 122 in FIG. 7), filters 116, and the like.

Further, the head 108 is configured to pivot in relation to the handle 102 as pressure is applied to the device 100 as well as contours of the surface to which the device 100 is applied change. The head 108 may be able to pivot up/down (vertically) and side to side (horizontally).

Depending on the pivot mechanism used, vertical and horizontal movement may be achieved simultaneously.

As described herein, it is preferable to use a topical agent or other liquid type agent in conjunction with the treatment device 100. As such, the vacuum feature has a foam based filter 116 to prevent suctioning of the topical agent into the device 100 thereby preventing the device 100 from becoming damaged. Such foam may be a polyethylene or other suitably dense foam that freely permits the passage of air or gasses (to create suction) while preventing the uptake of the generally liquid, gel, or amorphous topical agent(s).

Figure 8:
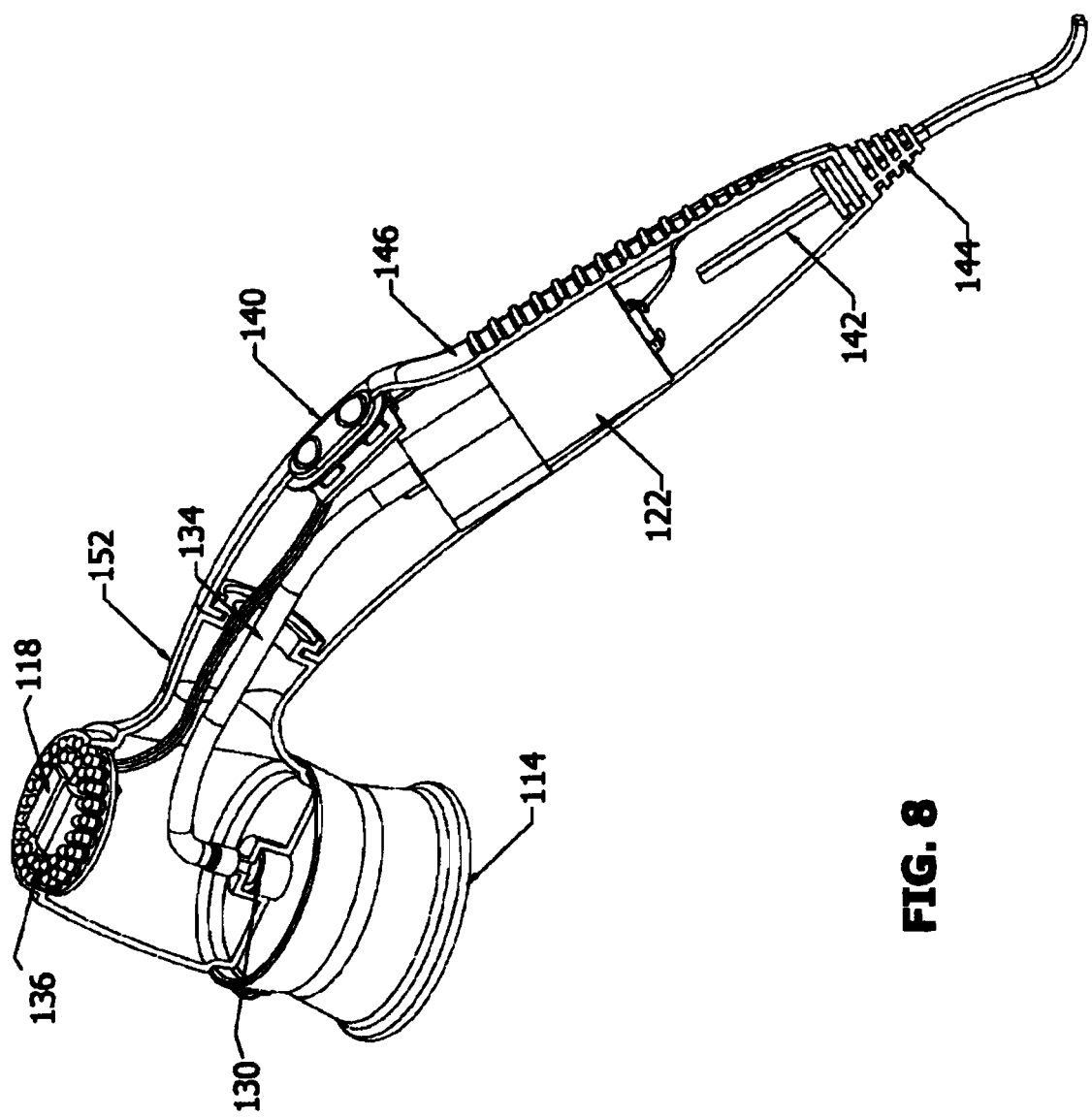
FIG. 8 illustrates a cross-sectional view of an embodiment of the present invention.
Figure 9:
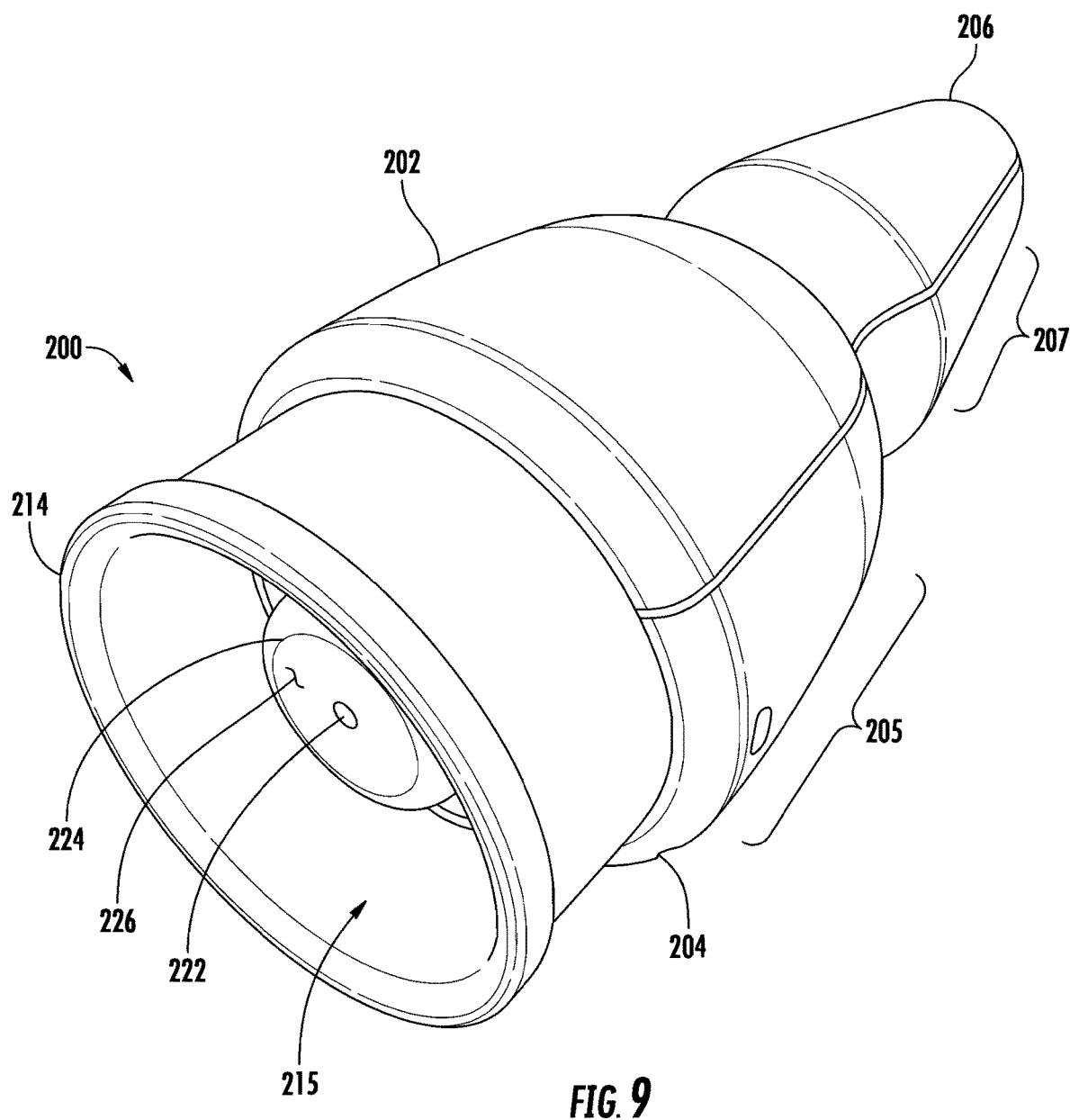
FIG. 9 illustrates a perspective view of an alternative embodiment of the present invention.
Figure 10:
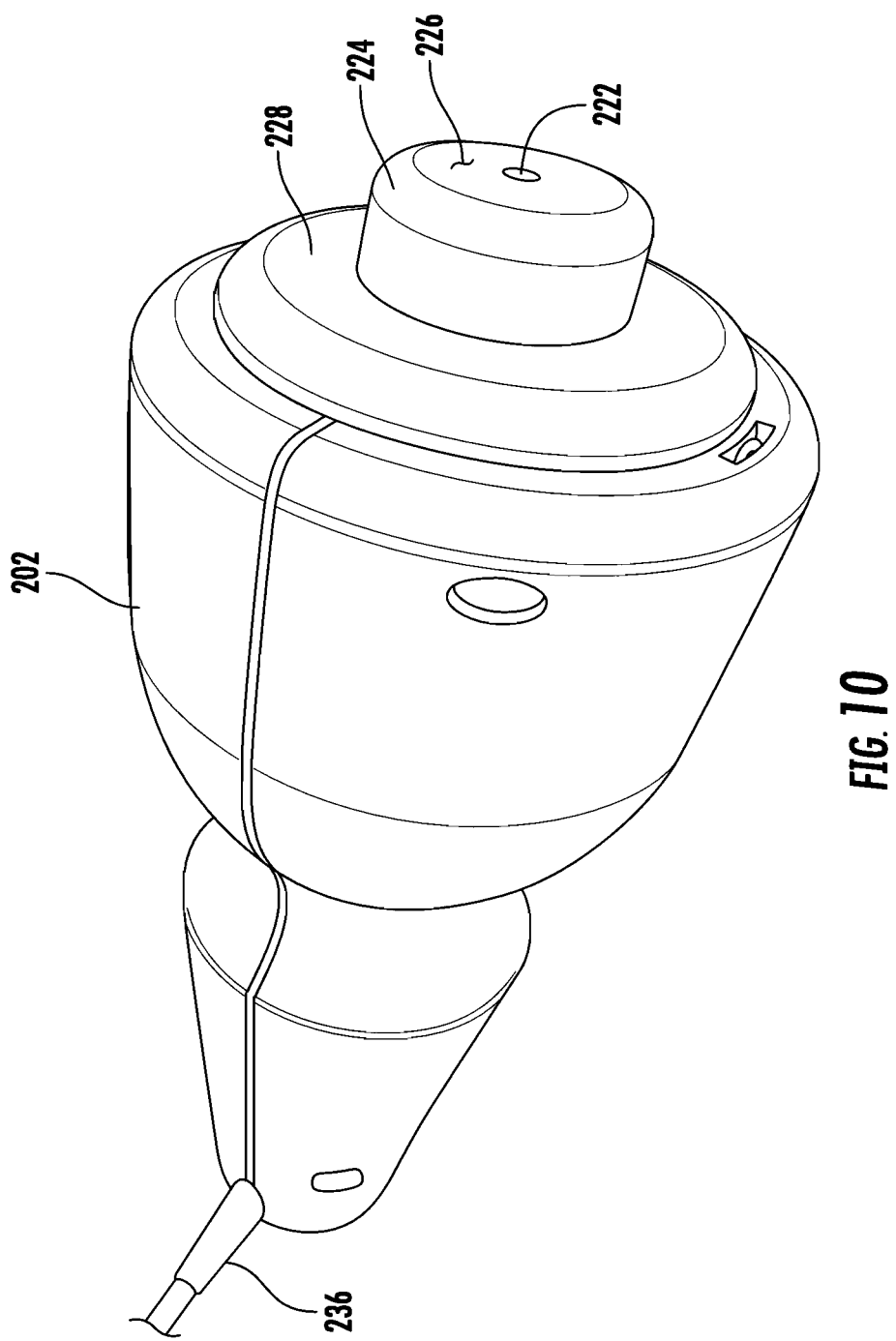
FIG. 10 illustrates a perspective view of the invention shown in FIG. 9, with the cap removed.
Figure 11:
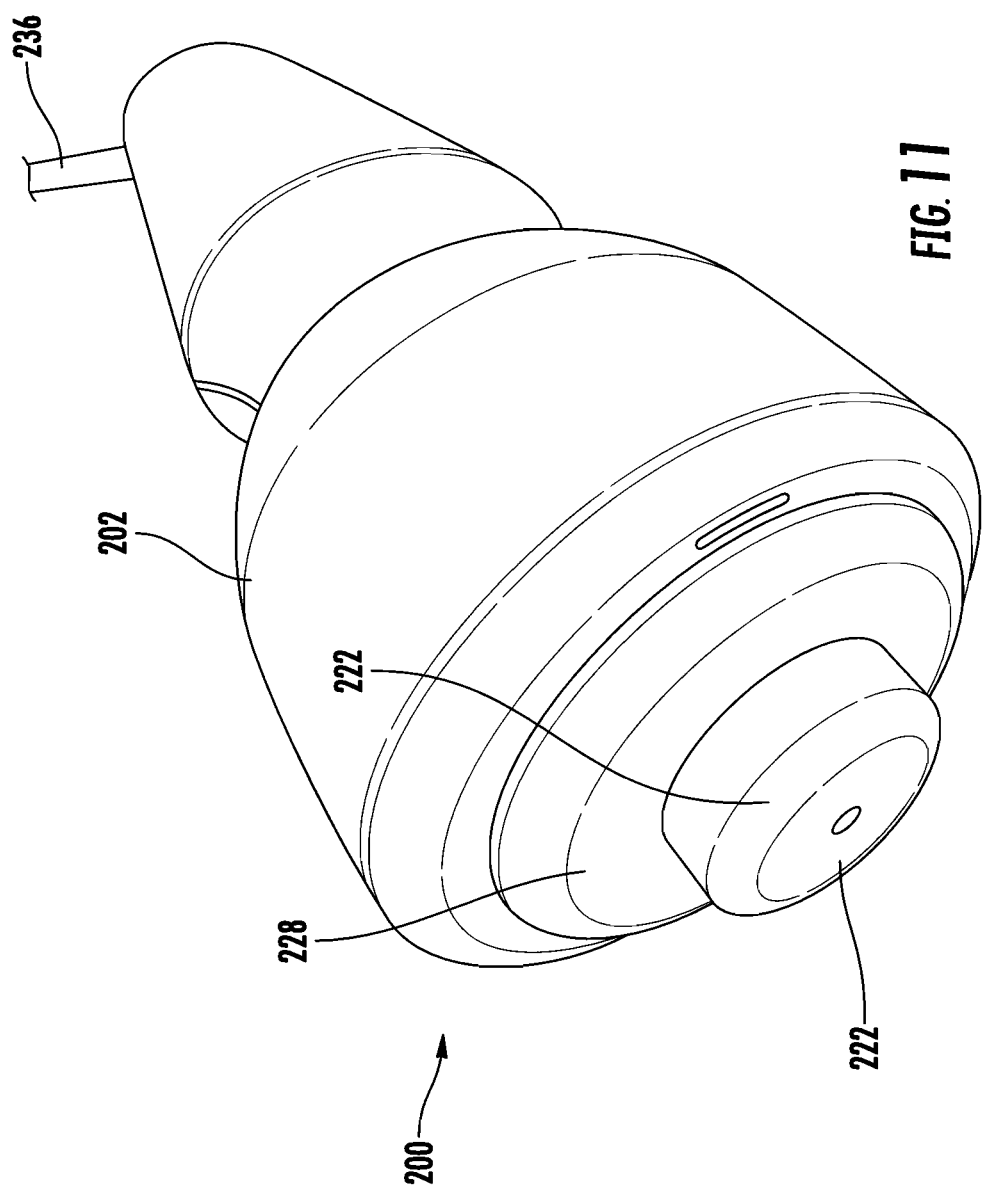
FIG. 11 is an alternative perspective view of the invention shown in FIG. 9, with the cap removed.
Figure 12:
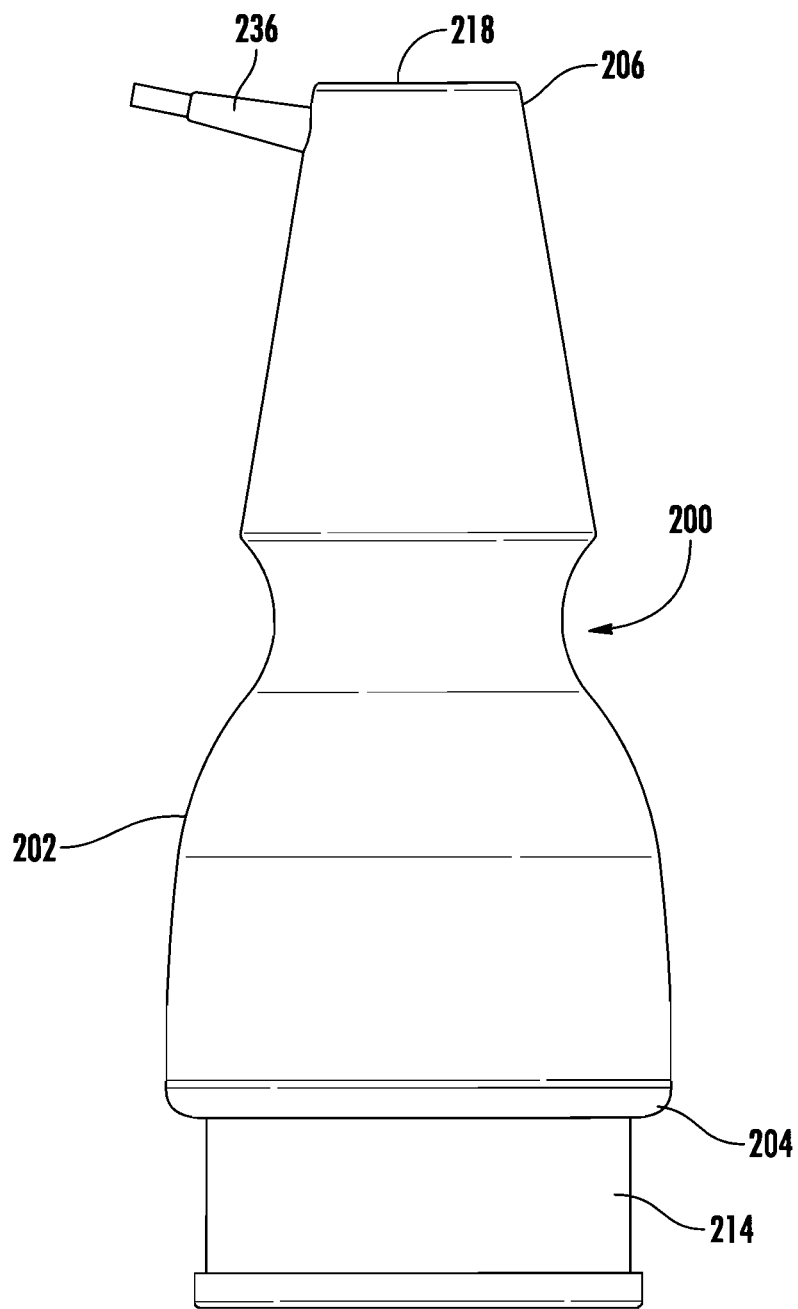
FIG. 12 is a side view of the invention shown in FIG. 9.
Figure 13:
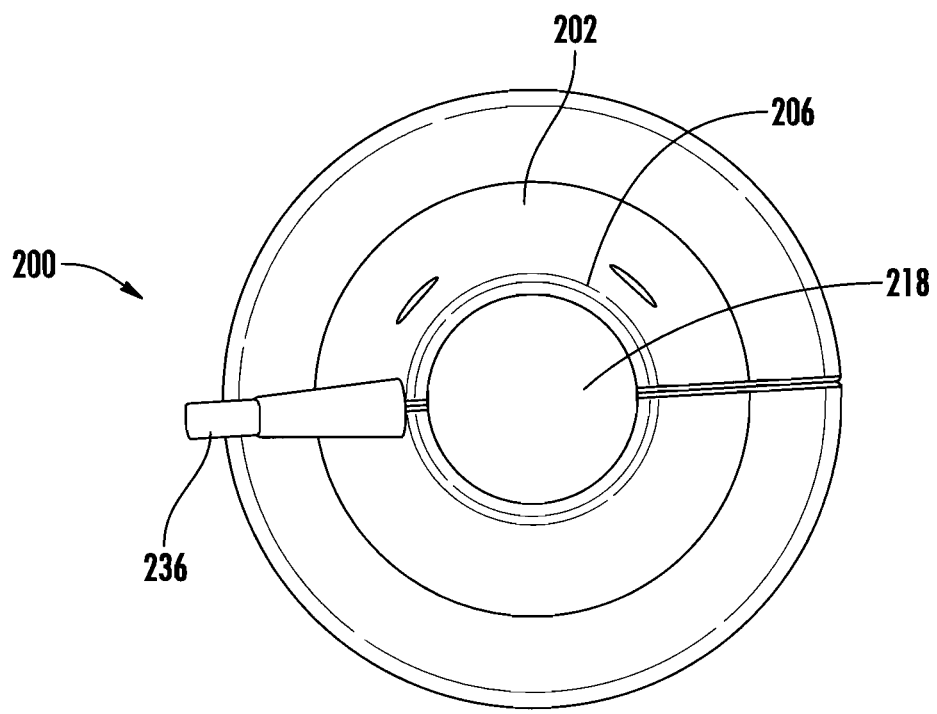
FIG. 13 is a top view of the invention shown in FIG.
Figure 14:
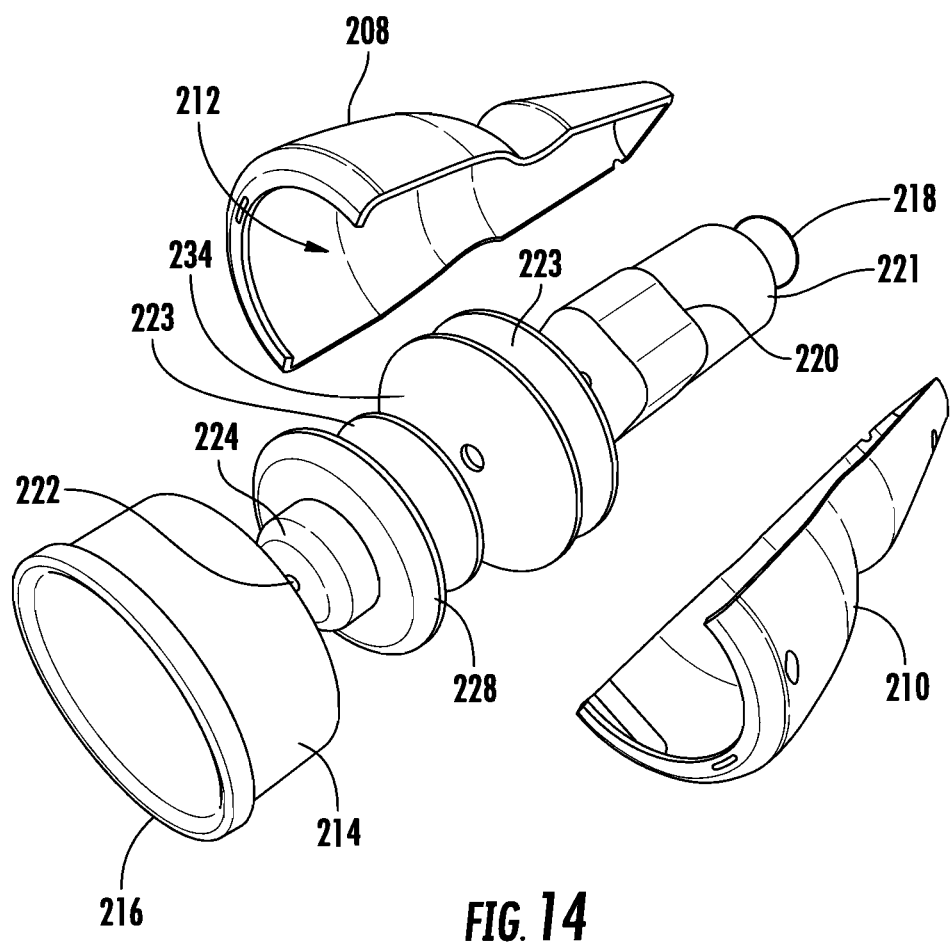
FIG. 14 is an exploded view of the invention shown in FIG. 10.
Figure 15:
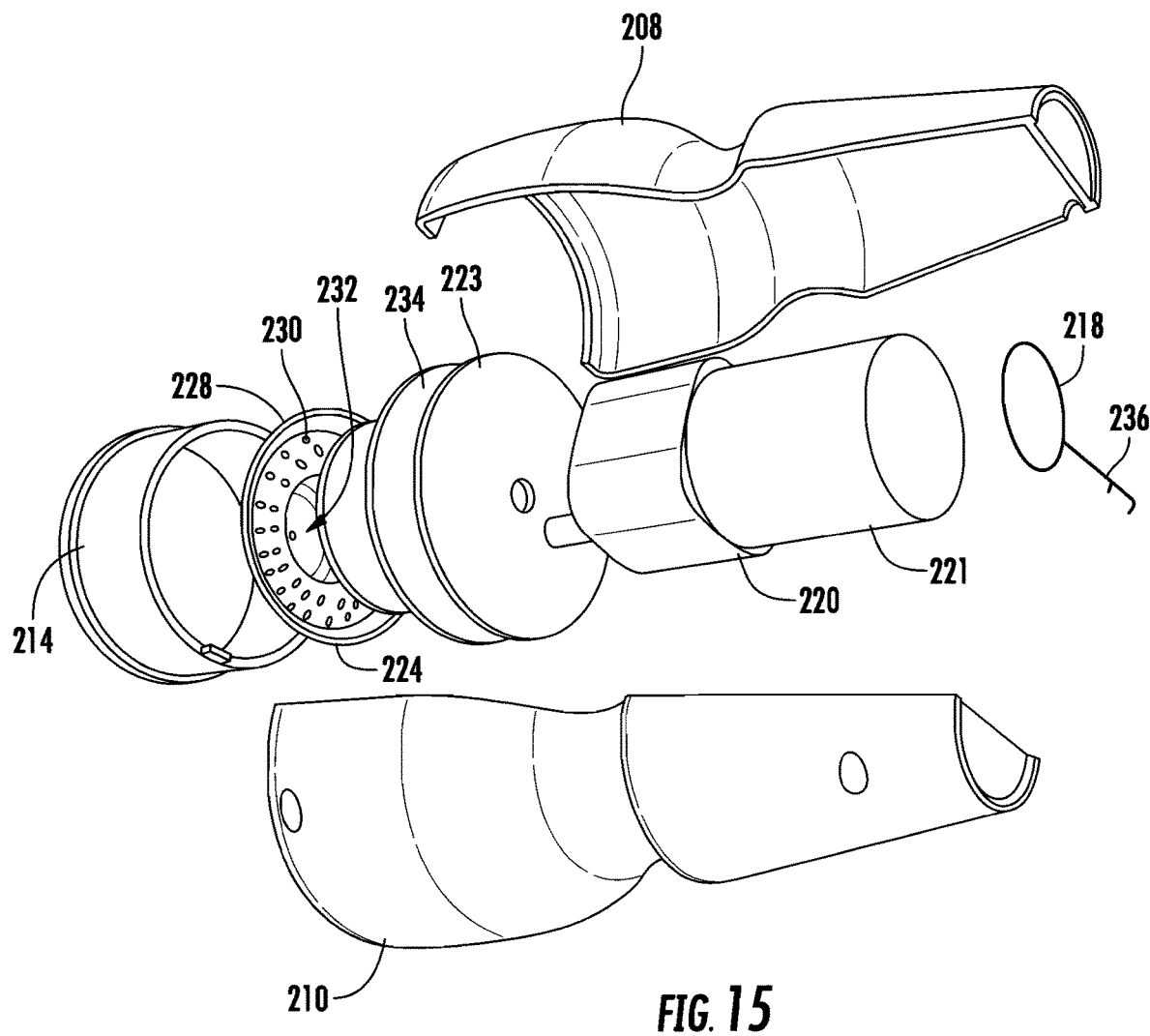
FIG. 15 is an alternative perspective view of the invention shown in FIG. 9.

The vacuum structures, as shown cross sectionally in FIG. 8, are on the bottom 112 of the head 108 and the ultrasonic transducer 118 and light sources 120 are located on a top 110 of the head 108. The vacuum side of the head 108 has a removable cup 114 to allow suction created by the vacuum (motor 122) to draw tissue upwards into and past the bottom plane of the removable cup 114. The removable cup 114 further has a slot 124 (see FIG. 7), via which the filter 116 can be removed or positioned to cover the vacuum port 130. The filter 116 may cover all or some of the port(s) and may be configured/shaped to the size and shape of the removable cup 114. Further, conventional locking mechanisms may be used to retain the filter 116 once positioned within the slot 124.

The edges or bottom perimeter of the removable cup 114 are rounded to promote a smooth sliding or movement across a skin surface. In some embodiments, additional external structures such as bearings may be used to facilitate the smooth movement across the skin surface. In some embodiments, a retaining ring may be coupled or uncoupled to this perimeter to allow for changing of the filter 116 and other maintenance of the device.

Behind the filter 116, there may be at least one and preferably a plurality of vacuum holes or ports 130 via which suction or a vacuum is created. The ports 130 are positioned to create sufficient suction of the skin while, in some embodiments, further holding the filter 116 in position. In some embodiments, a user may be able to activate or deactivate certain areas of the vacuum and the ports 130 therein to create a custom suction pattern and treatment. The vacuum may be created by a motor 122 contained within the device 100 or may require connection to such a motor or suction creating device. The device 100 may operate of a standard line voltage (power cord 142 and power cord anchor 144) or may other power sources including rechargeable or non-rechargeable batteries.

On a top surface 110 of the head 108 of the device 100 may be the ultrasonic transducer 118 and a light source array comprising a plurality of light sources 120. The ultrasonic transducer 118 may be configured to emit waves at a frequency of about 90 kc to about 950 kc. The light sources 120, as noted, may be any number and type of light emitting device including but not limited to LEDs, OLEDs, and the like. In a preferred embodiment, LEDs are utilized and emit light in a range of about 625 nm to about 725 nm and more preferably about 660 nm. Further light sources 120 may be employed that emit light in a range of about 900 nm to about 1000 nm and more preferably about 950 nm. In some embodiments, the light sources 120 and ultrasonic transducer 118 are operational simultaneously, whereas in other embodiments the light sources 120 and ultrasonic transducer 118 operate singularly.

As shown in FIG. 8, the light sources 120 may be arranged in an array comprising about twelve LEDs configured to emit a "red" wavelength of light and about twelve LEDs configured to emit a "near infrared" (IR) wavelength of light. In other embodiments, there may be as few as four light sources 120 or as many as fifty light sources 120 comprising each wavelength type. Each of the types of light sources 120 may be clustered, linearly arranged, or otherwise arranged to provide coverage to the user as needed. In some embodiments, the light sources 120 are interspersed with one another and each light source 120 emits a particular wavelength of light which may be the same or different as the light sources 120 directly proximate to it.

Further, the light sources 120, as shown in FIG. 7, may be coated or covered in an epoxy or other optically clear covering 128. This protects the light sources 120 and ultrasonic transducer 118 while still allowing the light sources 120 to be effective. It is preferable that any epoxy used is an optically clear epoxy to prevent interference with the light emitted by the light sources 120.

The present treatment device 100 may also be used in various methodologies to form treatment regiments for people afflicted with cellulite. The precise methodology used may depend on the user's needs as well as the device/topical agent parameters and qualities. Below is described but one of the methodologies that may be employed with the present invention. The below methodology is presented for exemplary purposes only and is not intended to limit the scope of the potential methodologies employed.

In a first step, a user may gently exfoliate the stratum corneum of the skin in the area to be treated. This will allow a proprietary or other topical agent to better penetrate the desired treatment area. Various exfoliates may include but are not limited such topicals as a pumpkin scrub, about 10% glycolic foam, or any other degreasing chemical or mechanical agent.

In a second step, a user may apply the topical agent which contains ingredients to achieve localized fatty breakdown, stimulate cellular metabolism, increase blood flow, reduce tissue inflammation and stimulate collagen. In one embodiment, the topical agent is a phosphatidylcholine based agent. The user may then apply the side of the head of the device with the light sources and ultrasound transducer to the skin. It is preferable that the user keep contact with the skin and slide the device slowly over the treatment area until the topical has fully absorbed by the skin.

In a third step, a user may apply the vacuum side of the device to the skin to achieve a gentle suction of the skin surface and underlying tissues into the device while keeping enough lubricant on the skin to gently slide or glide the device around the treatment area. This gentle manipulation of the tissue will assist in increasing the extensibility and/or length of the connective septae.

Referring now to FIGS. 9-14, an alternative embodiment of device 100, referred to as device 200, is shown. The device 200 is a hand held device configured to self-treat one or more anatomical or physiological defects that exist to create the cellulite appearance, including 1) poor vascular circulation in the area effected, 2) loss of collagen fibers which creates poor dermal-epidermal layers and permits the "orange peel" look that is common in cellulite effected skin, and 3) connective tissue bands form septa that hold the fat cells in a "locked in" status, which makes them appear as small beads and dimples under the skin. The device treats each one of these defects specifically through the use of light, vacuum, and ultrasound energy.

With regards to poor vascular circulation, proper blood flow is essential to maintaining healthy tissue. Among other things, proper blood flow builds collagen, carries away toxins, creates oxygenation in tissues which permits the proper balance of nutrients, vitamins, minerals, proteins and enzymes. Use of LED lights in accordance with embodiments of the invention helps alleviate poor vascular circulation.

When the skin layers lose too much collagen, a vital protein, the skin thins out. In addition, loss of collagen may result in loss of elasticity, revealing defects from the deeper layers, like fascia, muscle and fat. Collagen is also important in maintaining the wound healing qualities of the skin layers. Use of ultrasound in accordance with embodiments of the invention stimulates blood flow, which can reduce painful conditions and increase the uptake of valuable nutrients that are responsible for proper cellular responses. Too much ultrasound energy could result in internal burns. Too little ultrasound energy could result in the treatment will be useless. The energy settings used in accordance with embodiments of the invention are designed for treating cellulite.

When there is poor circulation of blood and loss of collagen, the body forms tissue septa because the connective bands develop as a form of desiccated tissue rather than healthy, collagen rich tissue. This is an example of healthy turnover of all cells in the body at programmed rates. It is called apoptosis. Without this normal turnover of all cells, the bands lock in place the fat cell and produce a very unsightly image known as orange peel skin with dimples and lumps. Use of vacuum in accordance with embodiments of the invention permits separation and breakdown of the connective bands, thereby repairing the defect in the bands. The action of suction in a constant pulse pattern with a catch and release concept in accordance with embodiments of the invention provides effective breakdown without pain to the user.

The device 200 is configured to provide a combination of light energy, ultrasonic energy, and vacuum to an object, such as when applied to the skin surface, to alleviate one or more disorders, such as poor vascular circulation, loss of collagen, and issues related to septa. The device 200 includes a main body 202 having a first end 204 and a second end 206. The main body 202 may be defined by an upper or head portion 205, shown having a generally cylindrical shape and a lower or tail portion 207, shown having a conical or frustoconical shape. The lower or tail portion 207 may be sized and shaped for easy gripping and holding by a user.

The main body 202 may be made of a first housing portion 208 and a second housing portion 210, which, when secured together, enclose an interior 212. The interior 212 is sized and shaped to store within one or more components that drive the device 200 functionalities. Removably attached to the first end 204 is a vacuum cup or ring 214. The vacuum cup or ring 214 may be sized and shaped to allow suction to draw tissue upwards into and past the bottom plane of the removable vacuum cup or ring 214. The edges or bottom perimeter 216 of the removable vacuum cup or ring 214 may be rounded to promote a smooth sliding or movement across a skin surface. Alternatively, the vacuum cup or ring 214 may be integrally formed to the main body 202. The second end 206 may include a control button 218 to power the device 200 to the "ON", or operating position, or to the "OFF" position. The removable vacuum cup or ring 214 is positioned on or secured to the main body 202 to allow light, ultrasound energy, and vacuum to be directed toward and/or within the interior portion area 215 of the removable vacuum cup or ring 214, thus focusing each to a particular area during operation of the device 200, and therefore to a treatment site during treatment as well.

The interior 212 of the main body 202 includes a vacuum pump 220 (with motor 221) which is operationally connected to a vacuum port 222 to generate suction. A cooling fan or disc 223 may be used for cooling the pump 220 or motor 221. The interior 212 further includes an ultrasonic transducer 224 having an external surface 226 configured to produce ultrasonic energy. The ultrasonic transducer 224 is positioned to extend out past the first end 204, positioning the external surface 226 to extend at least partially within the vacuum cup or ring 214 when the vacuum cup or ring 214 is attached. The vacuum port 222 may be positioned within the ultrasonic transducer external surface 226, thus extending at least partially within the vacuum cup or ring 214 when the vacuum cup or ring 214 is attached as well.

Positioned adjacent to and behind the ultrasonic transducer 224 is a light producing lens 228. The light producing lens 228 may include one or more light sources 230, such as one or more light emitting diodes (LEDs). The LEDs are arranged so that light emitted therefrom is directed towards the ultrasonic transducer external surface 226 and the area within the vacuum cup or ring 214. The light producing lens 228 may include an opening 232 sized and shaped to allow a portion of the ultrasonic transducer 224 to pass there through. The light sources 230 may be any number and type of light emitting device including, but not limited to, LEDs, OLEDs, and the like. In a preferred embodiment, the LEDs utilized emit light in a range of about 625 nm to about 725 nm, and more preferably about 660 nm. Further, light sources 230 may be employed that emit light in a range of about 900 nm to about 1000 nm, and more preferably about 960 nm. In an embodiment, device 200 may include light sources 230 that emit light in a range of about 625 nm to about 725 nm and light sources 230 that emit light in a range of about 900 nm to about 1000 nm. In a preferred embodiment, the device 200 comprises LEDs which emit light at 660 and 940 nanometers and are evenly distributed throughout.

In an embodiment, the device 200 may have one or more light sources 230 arranged in an array comprising one or more individual LEDs or arrays of LEDs configured to emit a "red" wavelength of light and one or more individual LEDs or arrays of LEDs configured to emit a "near infrared" (IR) wavelength of light. The light sources 230 may be clustered, linearly arranged, or otherwise arranged to provide coverage to the user as needed. In some embodiments, the light sources 230 are interspersed with one another, and each light source 230 emits a particular wavelength of light which may be the same or different as the light sources 230 directly proximate to it.

The functioning of one or more of the light sources 230, ultrasonic transducer 224, vacuum (via vacuum pump 220), or combinations thereof, may be controlled by a control unit, which may include a printed circuit board 234 having a processor with memory/storage. The printed circuit board 234 having a processor with memory/storage provides device 200 functions or operations. In an illustrative embodiment a person is exposed to light, vacuum and ultrasound according to:

Light treatment: The area to be treated is exposed to light of 625 nm to about 725 nm, and to light in a range of about 900 nm to about 1000 nm. Preferably, the area of treatment is exposed to light energy from one or more LEDs emitting light at 660 nm, and to one or more LEDs emitting light at 940 nm. The LED(s) output is preferably in the milliwatt range of 10 mW and emitted in a continuous wave mode.

Ultrasound treatment: The Ultrasound head 224 preferably runs at 1 MHz, 50/50 duty cycle, 0.5 seconds on and off. Output is slightly less than 1 watt/cm$^2$, such as 0.99 watts/cm$^2$ (0.495 W/cm$^2$ per cycle).

Vacuum treatment: The vacuum setting is powered on and never shuts off completely (continually pulsing). Application of vacuum, therefore, preferably cycles from a low of 2.0 to a max of 3.7 psi, with a 0.5 second cycle rate.

Each function of light, ultrasound, and vacuum treatment shuts off after a predetermined treatment time period. Preferably, the predetermined treatment time period is ten minutes. As such, light, ultrasound, and vacuum shuts off after ten minutes. The predetermined treatment time period may be greater or less than ten minutes. Additionally, a user may be exposed to multiple treatment time periods, such as two ten-minute treatment periods, three ten-minute treatment periods, four or more ten-minute treatment periods. While application of the three treatments (light, ultrasound, vacuum) may be programmed to terminate automatically, the control button 218 may include a start button, an off button, and vacuum release if one chooses to stop the vacuum, light, or ultrasound (individually or as a group), upon demand.

To aid in application of the device 200 to a treatment site, i.e. a person's skin, lubricant, such as a liquid, gel, or amorphous topical agent, may be used. To protect the vacuum pump 220 and motor 221 from becoming contaminated with the lubricating gel, the device 200 may include a filter 223, such as a paper or foam filter. Such foam may be a polyethylene or other suitably dense foam that freely permits the passage of air or gasses (to create suction) while preventing the uptake of the generally liquid, gel, or amorphous topical agent(s).

The device 200 may operate, i.e. the production of light, ultrasound energy, or vacuum, via standard line voltage using a power cord 236. Alternatively, the device 200 may operate using rechargeable or non-rechargeable batteries. While the vacuum is described as being created by a vacuum pump 220 with motor 221 placed within the device 200, vacuum production may be generated via connection to a motor or suction creating device located outside of the device 200.

The methods and settings described for the embodiment of device 200 are applicable to device 100.

Although this invention has been described with a certain degree of particularity, it is to be understood that the present disclosure has been made only by way of illustration, and that numerous changes in the details of construction and arrangement of parts may be resorted to without departing from the spirit and the scope of the invention.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of improving an appearance of cellulite comprising:
   exposing an area of skin of an individual to a combination of light energy, ultrasound energy, and vacuum as a treatment period;
   providing, during said treatment period, a graduated vacuum pressure to said individual, said vacuum pressure continually on and cycling from a low of 2.0 psi to a high of 3.7 psi, with a 0.5 second cycle rate;

providing, during said treatment period, said light energy to said area of skin of said individual, said light energy emitted from one or more light sources which emit light in a range of about 625 nm to about 725 nm, in a range of about 900 nm to about 1000 nm, or in a range of about 625 nm to about 725 nm and in a range of about 900 nm to about 1000 nm;

providing, during said treatment period, said ultrasound energy to said area of skin of said individual, said ultrasound energy being applied at the same time as exposure to said light, and cycling on and off.

2. The method of improving the appearance of cellulite according to claim 1, wherein said one or more light sources is one or more light emitting diodes (LEDs).

3. The method of improving the appearance of cellulite according to claim 2, wherein said one or more LEDs emit said light at 660 nm.

4. The method of improving the appearance of cellulite according to claim 2, wherein said one or more LEDs emit said light at 940 nm.

5. The method of improving the appearance of cellulite according to claim 2, wherein said one or more LEDs emit said light at 660 nm, and one or more LEDs emit said light at 940 nm.

6. The method of improving the appearance of cellulite according to claim 2, wherein said one or more LEDs have an output of 10 mW.

7. The method of improving the appearance of cellulite according to claim 1, wherein said ultrasound energy is 1 MHz.

8. The method of improving the appearance of cellulite according to claim 1, wherein said ultrasound energy is less than 1 watt/cm$^2$.

9. The method of improving the appearance of cellulite according to claim 1, wherein said ultrasound energy is applied at 0.5 seconds on and off interval cycles.

10. A method of improving an appearance of cellulite comprising:

using an electronic device to expose an individual to a combination of light energy treatment, ultrasound energy treatment, and vacuum treatment for a treatment time period, said electronic device having a vacuum cup;

said light energy treatment, applied during said treatment time period, comprising exposing said individual to light energy emitted from one or more light emitting diodes (LEDs) which emit light in a range of about 625 nm to about 725 nm, in a range of about 900 nm to about 1000 nm, or in a range of about 625 nm to about 725 nm and in a range of about 900 nm to about 1000 nm;

said ultrasound energy treatment, applied during said treatment time period, comprising exposing said individual to ultrasound energy which runs at 1 MHz, cycling on and off during said treatment time period; and said vacuum treatment, applied during said treatment time period, comprising exposing said individual to a graduated pressure by fitting said vacuum cup to an area of skin and creating a vacuum pressure within said vacuum cup, said vacuum pressure continually on and cycling from a low of 2.0 psi up to a high of 3.7 psi, with a 0.5 second cycle rate.

11. The method of improving the appearance of cellulite according to claim 10, wherein said treatment time period is ten minutes.

12. The method of improving the appearance of cellulite according to claim 10, wherein said light energy treatment comprises exposing said individual to said light energy at 660 nm and 940 nm.

13. The method of improving the appearance of cellulite according to claim 10, wherein said ultrasound energy treatment on/off cycle is 0.5 seconds on and 0.5 seconds off.

14. The method of improving the appearance of cellulite according to claim 10, wherein said ultrasound energy treatment output is less than 1 watt/cm$^2$.

15. The method of improving the appearance of cellulite according to claim 10, wherein said individual is exposed to a combination of light energy treatment, ultrasound energy treatment, and vacuum treatment for one or more additional treatment time periods.

\* \* \* \* \*